(12) United States Patent
Nakahara et al.

(10) Patent No.: US 6,695,928 B1
(45) Date of Patent: Feb. 24, 2004

(54) METHOD FOR PRODUCTION OF (METH) ACRYLIC ACID AND/OR (METH)ACRYLIC ESTERS

(75) Inventors: Sei Nakahara, Himeji (JP); Takeshi Nishimura, Himeji (JP); Masatoshi Ueoka, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/516,680

(22) Filed: Mar. 1, 2000

(30) Foreign Application Priority Data

Mar. 2, 1999 (JP) ............................................. 11-054316

(51) Int. Cl.⁷ ................................................ B08B 3/00
(52) U.S. Cl. ........................... 134/26; 134/2; 134/22.1; 134/22.12; 134/22.17; 134/29; 134/35; 134/36; 134/40; 134/42; 203/8; 203/37; 203/DIG. 21
(58) Field of Search ................................ 134/2, 26, 29, 134/22.1, 22.12, 22.13, 22.17, 35, 36, 40, 42; 203/DIG. 21, 8, 37

(56) References Cited

U.S. PATENT DOCUMENTS

| | | | | |
|---|---|---|---|---|
| 3,865,628 A | * | 2/1975 | Callahan et al. | 134/2 |
| 4,904,309 A | * | 2/1990 | Komabashiri et al. | 134/42 |
| 5,728,272 A | | 3/1998 | Hammon et al. | 203/8 |
| 5,782,989 A | * | 7/1998 | Rueter | 134/22.19 |
| 6,210,536 B1 | * | 4/2001 | Grossi et al. | 203/8 |

FOREIGN PATENT DOCUMENTS

| WO | WO 99/20595 | 4/1999 |
|---|---|---|

* cited by examiner

*Primary Examiner*—Randy Gulakowski
*Assistant Examiner*—M. Kornakov
(74) *Attorney, Agent, or Firm*—Mathews, Collins, Shepherd & McKay, P.A.

(57) ABSTRACT

A method for the production of (meth)acrylic acid and/or a (meth)acrylic ester is provided. This method for the production of (meth)acrylic acid and/or a (meth)acrylic ester includes washing the device constructed for the production thereof with a basic solution and subsequently rinsing them with a solvent for the purpose of removing solid substances such as polymer and precipitate which occur during the production of (meth)acrylic acid and/or a (meth)acrylic ester.

19 Claims, No Drawings

METHOD FOR PRODUCTION OF (METH) ACRYLIC ACID AND/OR (METH)ACRYLIC ESTERS

BACKGROUND OF THE INVENTION

1. Field of the Invention

This invention relates to a method for the production of (meth)acrylic acid and/or (meth)acrylic esters. More specifically, it relates to a method for the production of (meth)acrylic acid and/or (meth)acrylic esters, characterized by removing solid substances such as polymer and precipitate which adhere to devices and pipes to be used for the production of (meth)acrylic acid and/or (meth)acrylic esters.

2. Description of the Related Art

It is well known that (meth)acrylic acid and/or (meth)acrylic esters are susceptible to polymerization and, during the process of production thereof, often generate polymers and oblige relevant devices to stop. It has been universally known to cope with this trouble by adding a polymerization inhibitor such as hydroquinone and phenothiazine to the relevant raw material prior to the production of (meth)acrylic acid and the like or performing a surface treatment on the relevant devices for the purpose of preventing solid substances such as polymer and precipitate from adhering to the devices. None of these measures, however, has attained perfect prevention of occurrence and adhesion of solid substances such as polymer and precipitate.

U.S. Pat. No. 5,728,272 discloses a method which, with a view to facilitating the removal of generated polymer, comprises stopping and washing the relevant devices while the cumulative amount of a generated polymer is small. The effect of this method in preventing the occurrence of solid substances such as polymer and precipitate, however, does not deserve to be rated fully satisfactory.

SUMMARY OF THE INVENTION

The object of the present invention is the provision of a method for inhibiting the occurrence of solid substances such as polymer and precipitate during the process for production of (meth)acrylic acid and/or (meth)acrylic esters, particularly for inhibiting the occurrence and adhesion of solid substances such as polymer or polymerized material and precipitate on the heated surfaces of a boiler and a jacket.

Further by this invention, the formation of (meth)acrylic acid due to the decomposition of an ester during the process for purification of (meth)acrylic ester can be effectively prevented.

The present inventors have found by their study that the occurrence and adhesion of such solid substances as polymer and precipitate which are formed during the process for production of (meth)acrylic acid and/or (meth)acrylic esters and the formation of (meth)acrylic acid due to the decomposition of an ester during the process of purification of (meth)acrylic esters are caused by the basic substance which emanates in a small amount from a basic solution used in washing devices and reaches the respective sites of production and purification. This invention has been perfected as a result.

Specifically, according to the invention it can provide a method for the production of (meth)acrylic acid and/or (meth)acrylic esters characterized by, when the production thereof is stopped, washing the device constructed for producing (meth)acrylic acid and/or (meth)acrylic esters with a basic solution for the purpose of removing solid substances such as polymer and precipitate formed on the surfaces of a flow way of(meth)acrylic acid and/or (meth)acrylic esters in the device during the course of the production and subsequently rinsing the device with a solvent.

According to the method of this invention, namely by washing devices, pipes, and the like with a basic solution during the process of production of (meth)acrylic acid and/or (meth)acrylic esters and thereafter rinsing them with a solvent, it is made possible to remove such solid substances as polymer and precipitate which adhere to the parts of devices and pipes in a short time and realize protracted operation of the process for the production of (meth)acrylic acid and/or (meth)acrylic esters.

Particularly in the case of the process for the production of (meth)acrylic esters, the formation of (meth)acrylic acid due to the decomposition of such esters can be effectively prevented.

The above and other objects, features, and advantages of the present invention will become clear from the following description of the preferred embodiments.

DESCRIPTION OF THE PREFERRED EMBODIMENTS

The expression "process for the production of (meth) acrylic acid and/or (meth)acrylic esters" as used herein refers to a step of cooling a (meth)acrylic acid-containing gas obtained by the catalytic vapor phase oxidation of a propylene and/or acrolein containing gas with a solvent and collecting (absorbing) the cooled gas by counter flow washing, a step of recovering (meth)acrylic acid from the collected (absorbed) mixture of the solvent and the (meth) acrylic acid (JP-B-06-15,496), and a step of esterifying the (meth)acrylic acid and recovering the resultant (meth) acrylic ester (JP-A-10-231,275). Examples of the (meth) acrylic ester may include alkyl acrylates such as hydroxyethyl (meth)acrylate, hydroxypropyl (meth)acrylate, glycidyl (meth)acrylate, butyl (meth)acrylate, methyl (meth) acrylate, ethyl (meth)acrylate, and 2-ethylhexyl (meth) acrylate.

The process which continues till recovery of the formed (meth)acrylic acid comprises devices such as an absorption column for absorbing (meth)acrylic acid from the reaction gas of (meth)acrylic acid, a stripping column, an extraction column, a solvent separation column, an azeotropic separation column in which dehydration is performed with an azeotropic solvent, an acetic acid separation column, a high boiling component separation column for removing high boiling substances such as a stabilizer, a rectification column, and a storage tank, a condenser, a re-boiler, a strainer, and a pump which are accessories of the devices annexed to the upper, middle or lower part thereof, and pipes for example between the columns, and between any of the columns and any of the accessories thereof mentioned above.

Then, the process which continues till recovery of a (meth)acrylic ester comprises devices such as a reaction column or tower for the esterification of (meth)acrylic acid with an alcohol, an ester extraction column, a more volatile component separation column, a rectification column, and a storage tank, a condenser, a re-boiler, a strainer, and a pump which are accessories of the devices annexed to the upper, middle or lower part thereof, and pipes for example between the columns, and between any of the columns and any of the accessories thereof mentioned above.

The distillation column to be used in this invention is not particularly discriminated but has only to be capable of effecting distillation. Examples of the distillation column may include a packed column, a tray column, a wetted-wall column, and a spray column. The term "distillation column" as used herein means to include accessories for a distillation column such as a heat exchanger, a condenser, a re-boiler, and a jacket. Among other items mentioned above, the device is preferred to include a distillation column and accessories of a distillation column such as a heat exchanger, a re-boiler, and a jacket.

In general, polymer and precipitate adhere to the surface of a flow way of (meth)acrylic acid and/or an (meth)acrylic ester in the state of liquid and/or vapor in the devices, accessories, and pipes between them. In the present invention, the adhered polymer and precipitate can be removed by means of a special washing in particular without overhauling the system of devices, accessories, and pipes between them constructed for the production of (meth) acrylic acid and/or an (meth)acrylic ester.

The basic solution to be used in this invention is not particularly discriminated but is only required to be a solution of a basic substance. It is preferred to be an aqueous solution of at least one member selected from the group consisting of an oxide, hydroxide, carbonate, and hydrogen carbonate of an alkali metal such as lithium, sodium, potassium, and rubidium, an oxide and hydroxide of an alkaline earth metal such as magnesium, calcium, strontium, and barium, and a mixture thereof. The basic substance is preferred to be at least one member selected from the group consisting of an oxide, hydroxide, carbonate, and hydrogen carbonates of an alkali metal and particularly preferred to be a hydroxide thereof. Among other alkali metals, sodium or potassium proves to be favorable.

Though the conditions fit for washing with a basic solution may be arbitrarily selected in view of such factors as the ease of solution of solid substances such as polymer and precipitate which adhere to the articles given to be washed, the washing temperature to be used in the bottom of a column may be proper in the range of from 50° C. to the boiling point of the basic solution containing the polymer and precipitate peeled off, preferably from 80° C. to the boiling point. Particularly, the alkali steaming which uses the basic solution in a boiling state proves appropriate for the purpose of washing. The washing time is not particularly discriminated. Though several hours generally suffice to produce the effect, the washing may be performed till the adhering solid substances are thoroughly peeled or dissolved. Though the pressure to be applied during the course of washing is not limited particularly, the washing is preferred to be carried out under a reduced pressure for the purpose of enhancing the flowability of the basic solution inside the device such as a distillation column. The washing performed under the reduced pressure results, for example, in increasing the effect of washing the rear side of the tray in the distillation column and ultimately curtailing the washing time. With a view to heightening the effect of the reduced pressure on the washing, the washing may be properly carried out under the pressure in the range of 100–900 hPa, preferably 150–300 hPa.

Though the mechanism of the separation or dissolution of the solid substances has not been elucidated, it may be logically explained by supposing that the ester group is saponified or the carboxyl group is converted into a salt and the resultant product is gradually dissolved in the basic solution.

When the basic solution is one member or a mixture of two or more members selected from the group consisting of aqueous solutions of an oxide, hydroxide, carbonate, and hydrogen carbonate of an alkali metal and an oxide and hydroxide of an alkaline earth metal, the concentration of the alkali metal and alkali earth metal compounds in the basic solution to be used for washing may be arbitrarily selected in respect of the ease of solution of solid substances such as polymer and precipitate which adhere to the articles being washed. It is be preferred to be in the range of 1 to 10 wt. %. Though the pressure to be applied to the site of washing is not specifically discriminated, the washing is preferred to be performed under a reduced pressure for the purpose of enhancing the flowability of the solvent within the device such as the interior of a distillation column. The washing carried out under a reduced pressure results in increasing the effect of washing the rear side of the tray in the distillation column and eventually curtailing the washing time. For the purpose of enhancing the effect of the reduced pressure on the washing, the washing may be properly carried out under a pressure in the range of 100–900 hPa, preferably 150–300 hPa.

The question whether the washing with the basic solution has been successfully performed can be confirmed by testing the distillation column for pressure loss or the heat exchanger for coefficient of heat transfer and overhauling and inspecting the device.

After the device has been washed with the basic solution, it is rinsed with a solvent. This solvent is not particularly discriminated but is only required to be capable of rinsing the detergent of an alkali metal and the like. Particularly, water is used advantageously as the solvent. Examples of the water properly used as the solvent may include deionized water, distilled water, and tap water. From the viewpoint of impurities such as sodium and calcium ions contained in water, the water to be used as the solvent may be preferred to have electric conductivity of not more than 10 mS/m, preferably not more than 1 mS/m (not including zero).

The conditions for rinsing with the solvent subsequent to the washing with the basic solution is not specifically discriminated. For the purpose of heightening the effect of washing, the washing temperature to be used in the bottom of the column may be properly in the range of 20° C. to the boiling point, preferably 50° C. to the boiling point, the more preferably 80° C. to the boiling point.

The washing with the aqueous solution of a basic substance is followed by the rinsing with water. Properly, the waste water which arises from the rinsing with water may have a pH value not exceeding 9, preferably falling in the range of 6–8 at 50° C. The waste water which emanates from the rinsing with water subsequent to the washing with the basic solution properly has a total content of the alkali metal and alkaline earth metal of not more than 50 mg/liter, preferably not more than 10 mg/liter. Particularly, it can decrease the formation of (meth)acrylic acid by decomposition of an ester thereof during the refining process of (meth)acrylate.

Further, before washing with the basic solution it can perform pre-washing with a solvent, particularly water. Especially when the amount of the polymer and precipitate to be purged by washing is large, the washing with the basic solution possibly swells the polymer to the extent of inflicting damage to the devices. This trouble may be avoided by preparatorily depriving the polymer of the part thereof which is soluble in the solvent. Though the conditions for the pre-washing is not particularly discriminated, the pre-washing temperature in the bottom of a column may fall in the range of 20° C. to the boiling point, preferably 50° C. to the boiling point, and more preferably 80° C. to the boiling point for the purpose of heightening the effect of pre-washing. The pressure applied during the course of pre-washing is not particularly discriminated. The pre-washing, however, may be preferably carried out under a reduced pressure for the purpose of enhancing the flowability of the solvent inside the device such as the interior of a distillation column. The pre-washing performed under a reduced pressure results in increasing the effect of washing the rear side of the tray in the distillation column and eventually curtailing the pre-washing time. For the purpose of heightening the effect of pre-washing under a reduced pressure, it may perform the pre-washing under a pressure in the range of 100–900 hPa, preferably 150–300 hPa.

EXAMPLES

Now, this invention will be described more specifically below with reference to examples. It should be noted that the following examples are intended to promote comprehension of the invention and not to limit this invention in any sense.

The electric conductivity of water was determined with an instrument made by Toa Denpa Kogyo K. K. in Japan and sold under a trademark designation of Conductivity Meter CM-60V, the contents of alkali metal and alkaline earth metal in water were determined with a plasma emission spectroanalyzer produced by Kyoto Koken K. K. in Japan and sold under a product code of UOP-1, and the coefficient of heat transfer was calculated as the numerical value found by dividing the quantity of heat by the heating area of the shell-and-tube type heat exchanger and temperature difference between process liquid and the heat medium. The quantity of acrylic acid in butyl acrylate was determined by the method of neutralization titration with NaOH.

Example 1

A distillation column provided with a shell-and-tube heat exchanger was adapted to separate water from an aqueous acrylic acid solution with methyl isobutyl ketone as an azeotropic solvent. The flow way of acrylic acid in the distillation column and the heat exchanger was adopted as an object of washing. The aqueous acrylic acid solution was obtained by the method disclosed in JP-B-60-32,615 (Example 1).

For the purpose of removing the polymer generated in the distillation column measuring 1 m in diameter and furnished with 40 shelving weirless perforated plates (using SUS 316 in the parts exposed to liquids and their vapor), an aqueous 8% sodium hydroxide solution was supplied from the top of the column with the aid of a refluxing line and a refluxing pump and the shell-and-tube heat exchanger was operated meanwhile to heat the aqueous sodium hydroxide solution under normal pressure (at 102° C.). Part of the liquid in the bottom of the column was continuously extracted while the supply of the aqueous 8% sodium hydroxide solution from the top of the column was continued and the liquid in the bottom of the column was kept in a boiling state. After the ensuant state lasted for two hours, the supply of the aqueous sodium hydroxide solution from the top of the column and the heating of the solution with the shell-and-tube heat exchanger were stopped and the aqueous solution was discharged from the interior of the column.

Subsequently, water was supplied from the top of the distillation column to effect rinsing (at 100° C.) similarly to the washing with the aqueous sodium hydroxide solution. The water used for rinsing had an electric conductivity of 15 mS/m at 25° C. The rinsing was stopped at the time that the waste water assumed a pH value of 8 (at 50° C.). The total content of alkali metal and alkaline earth metal in the waste water was found to be 25 mg/liter.

Then, the aqueous acrylic acid solution was subjected to distillation. Even after the elapse of 100 days of continued distillation, virtually no sign of increase in the pressure loss in the interior of the column and decrease in the coefficient of heat transfer of the shell-and-tube heat type exchanger was observed. When the distillation was stopped and the interior of the distillation column was inspected, a sign of formation of a small amount of polymer of the acrylic acid was observed. Then the column was found to permit the distillation to continue further.

Example 2

The distillation column was washed with an aqueous 8% sodium hydroxide solution and then rinsed with water in the same manner as in Example 1. The water used for the rinsing had an electric conductivity of 5 mS/m at 25° C. When the rinsing with water was stopped and the pH value of the waste water reached to 8 (at 50° C.), the total content of alkali metal and alkaline earth metal in the waste water was found to be 8 mg/liter.

Then, the aqueous acrylic acid solution was subjected to distillation. Even after the elapse of 100 days of continued distillation, virtually no sign of increase in the pressure loss in the interior of the distillation column and decrease in the coefficient of heat transfer of the shell-and-tube type heat exchanger was observed. When the distillation was stopped and the interior of the distillation column was inspected, a sign of formation of a small amount of polymer of the acrylic acid was observed. Then the column was found to permit the distillation to continue further.

Comparative Example 1

The distillation column was washed by following the procedure of Example 1 while omitting the rinsing with water subsequent to the washing with an aqueous 8% sodium hydroxide solution.

Then, the aqueous acrylic acid solution was subjected to distillation. The pressure loss in the interior of the column was found to increase and the coefficient of heat transfer of the shell-and-tube type heat exchanger to decrease within four days of starting the distillation. The distillation was then stopped and the interior of the column was inspected. Copious formation of the polymer of acrylic acid was found inside the distillation column and inside the shell-and-tube heat exchanger.

Comparative Example 2

The distillation column was washed with an aqueous 8% sodium hydroxide solution and then rinsed with water in the same manner as in Example 1. In this case, the rinsing with water was stopped when the pH value of the waste water reached to 10 (50° C.). The total content of alkali metal and alkaline earth metal in the waste water was found to be 40 mg/liter.

Then, the aqueous acrylic acid solution was subjected to distillation. The pressure loss in the interior of the column was found to increase and the coefficient of heat transfer of the shell-and-tube type heat exchanger to decrease within 20 days of starting the distillation. The distillation was then stopped and the interior of the column was inspected. Copious formation of the polymer of acrylic acid was found inside the distillation column and inside the shell-and-tube heat exchanger.

Example 3

A distillation column provided with a shell-and-tube heat exchanger was adapted to produce refined butyl acrylate from crude butyl acrylate deprived of volatile impurities. The flow way of butyl acrylate in the distillation column and heat exchanger was adopted as an object for washing. The crude butyl acrylate was obtained by the method disclosed in JP-B-06-86,406 (Example 1).

For the purpose of removing the polymer generated in the distillation column (using SUS 304 in the parts exposed to liquids and their vapor) measuring 1.2 m in diameter and packed with cascade miniature rings, water (having an electric conductivity of 0.5 mS/m at 25° C.) heated to 50° was supplied to the surface of the column exposed to the butyl acrylate and the vapor thereof while the shell-and-tube heat exchanger annexed to the distillation column was operated to heat water under normal pressure. Part of the liquid in the bottom of the column was continuously extracted while the supply of water from the top of the column was continued and the liquid in the bottom of the column was kept in a boiling state. After the ensuant state lasted for one hour, the water supplied from the top of the column was switched to an aqueous 4% sodium hydroxide solution. Then, the column was washed (at 101° C.) with an aqueous 4% sodium hydroxide solution in the same manner as in Example 1 and then rinsed (at 100° C.) with water. The water used for the rinsing had an electric conductivity of 0.5 mS/m at 25° C. The rinsing with water was stopped when the pH value of the waste water reached to 8 (at 50°). The total content of alkali metal and alkaline earth metal in the waste water was found to be 1 mg/liter.

Then, the crude butyl acrylate was subjected to distillation. Even after the elapse of 200 days of continued distillation, no sign of increase in the pressure loss within the column and decrease in the coefficient of heat transfer of the shell-and-tube heat exchanger was observed. The concentration of acrylic acid in the distilled butyl acrylate was not observed to increase. When the distillation was stopped and the interior of the distillation column was inspected, a sign of formation of a small amount of polymer of butyl acrylate was observed. Then the distillation column was found to permit the distillation to continue further.

Example 4

The distillation column was washed by following the procedure of Example 3 while using water having an electric conductivity of 15 mS/m for the ringing. When the rinsing was continued until the pH value of the waste water reached to 8 (at 50° C.), the total content of alkali metal and alkaline earth metal was found to be 30 mg/liter.

Then, the crude butyl acrylate was subjected to distillation. Even after the elapse of 120 days of continued distillation, no sign of increase in the pressure loss within the column and decrease in the coefficient of heat transfer of the shell-and-tube heat exchanger was observed. The concentration of acrylic acid in the distilled butyl acrylate was not observed to increase. When the distillation was stopped and the interior of the distillation column was inspected, a sign of formation of a small amount of polymer of butyl acrylate was observed. Then the distillation column was found to permit the distillation to continue further.

Comparative Example 3

The distillation column was washed with an aqueous 4% sodium hydroxide solution and then rinsed with water having an electric conductivity of 0.5 mS/m (25° C.) in the same manner as in Example 3. In this case, the rinsing was stopped when the pH value of the waste water reached to 10 (50° C.). The total content of alkali metal and alkaline earth metal in the waste water was found to be 30 mg/liter.

Then, butyl acrylate was subjected to distillation. After the elapse of 10 days of continued distillation, the acrylic acid concentration in the distilled butyl acrylate was observed to rise, the pressure loss in the column to increase, and the coefficient of heat transfer of the shell-and-tube heat exchanger to decrease. When the distillation was stopped and the interior of the distillation column was inspected, then copious formation of the polymer of butyl acrylate was observed inside the distillation column and inside the shell-and-tube heat exchanger.

Example 5

A distillation column provided with a shell-and-tube heat exchanger was adapted to separate water from the aqueous acrylic acid solution with toluene as an azeotropic solvent. The flow way of acrylic acid in the distillation column and heat exchanger was adopted as an object for washing. The aqueous acrylic acid solution was obtained by the method disclosed in JP-B-60-32,615 (Example 1).

For the purpose of removing the polymer generated copiously in the distillation column (using SUS 316 in the parts exposed to liquids and their vapor) measuring 1 m in diameter and furnished with 40 shelving weirless perforated plates, water (having an electric conductivity of 15 mS/m at 25° C.) heated to 50° was supplied to the surface of the column exposed to the aqueous acrylic acid solution and the vapor thereof while the shell-and-tube heat exchanger annexed to the distillation column was operated to heat water under normal pressure. Part of the liquid in the bottom of the column was continuously extracted while the supply of water from the top of the column was continued and the liquid in the bottom of the column was kept in a boiling state. After the ensuant state lasted for one hour, the water supplied from the top of the column was switched to an aqueous 4% potassium hydroxide solution, with the washing continued for four hours. Thereafter, the supply of the aqueous 4% potassium hydroxide solution from the top of the column and the heating thereof with the shell-and-tube heat exchanger were stopped and the aqueous 4% potassium hydroxide was discharged from the column. Subsequently, water having an electric conductivity of 0.5 mS/m (at 25° C.) was supplied from the top of the column to rinse the column in the same manner as when the aqueous 4% potassium hydroxide solution was used. When the rinsing was stopped at the time that the pH value of the waste water reached to 8 (at 50° C.) (after the elapse of about 2 hours), the total content of alkali metal and alkaline earth metal in the waste water was found to be 1 mg/liter.

Thereafter, the aqueous acrylic acid solution was subjected to distillation. Even after the elapse of 120 days of continued distillation, virtually no sign of increase in the pressure loss inside the column and decrease in the coefficient of heat transfer of the shell-and-tube heat exchanger was observed. When the distillation was stopped and the interior of the distillation column was inspected, then absolutely no sign of formation of the polymer of acrylic acid was observed.

Comparative Example 4

The distillation column was washed by following the procedure of Example 5 while omitting the pre-washing with water. When an aqueous 4% potassium hydroxide solution was supplied from the top of the column and the shell-and-tube heat exchanger annexed to the distillation column was operated to heat the aqueous 4% potassium hydroxide solution, then the polymer was swelled within 30 minutes of starting the heating and the distillation column was blocked and the washing could no longer be continued.

Example 6

Now, the case of distilling crude methacrylic acid containing high boiling impurities will be described here. The crude methacrylic acid was obtained by the method disclosed in JP-A-59-44,337 (Example 1).

For the purpose of purging a distillation column measuring 1.2 m in diameter and furnished with 30 shelving weirless perforated plates to expel the polymer generated therein, water (electric conductivity 5 mS/m (at 25° C.)) heated in advance to 50° C. was supplied from the top of the column and the shell-and-tube heat exchanger annexed to the distillation column was operated to heat the water under normal pressure. Part of the liquid in the bottom of the column was continuously extracted while the supply of water from the top of the column was continued and the liquid in the bottom of the column was kept in a boiling state. After the ensuant state lasted for two hours, the water supplied from the top of the column was switched to an aqueous 4% sodium hydroxide, with the washing continued for 6 hours. Subsequently, the supply of the aqueous 4% sodium hydroxide solution and the heating thereof with the shell-and-tube heat exchanger were stopped and the aqueous 4% sodium hydroxide was discharged from the column. Water (electric conductivity 5 mS/m at 25° C.) from the top of the distillation column was supplied to rinse with water in the same manner as when the washing was carried out with an aqueous 4% sodium hydroxide solution. When the rinsing with water was stopped at the time that the pH value of the waste water reached to 8 (at 50° C.), the total content of alkali metal and alkaline earth metal in the waste water was found to be 7 mg/liter.

Thereafter, crude methacrylic acid was subjected to distillation. Even after the elapse of 150 days of continued distillation, virtually no sign of increase in the pressure loss in the column and decrease in the coefficient of heat transfer of the shell-and-tube heat exchanger was observed. When the distillation was stopped and the interior of the distillation column was inspected, then the polymer of acrylic acid was formed in a small amount and the column was found to permit the distillation to be further continued.

Example 7

The distillation column was washed by following the procedure of Example 5 while setting the pressure in the distillation column at 250 hPa, the pre-washing time with water at 30 minutes, and the washing time with the aqueous potassium hydroxide solution at 2 hours.

When the washing was performed under the conditions mentioned above, the time at which the pH value of the waste water reached to 8 (at 50° C.) was about one hour after the start of the rinsing with water in the rinsing with water subsequent to the washing with the aqueous potassium hydroxide solution. The rinsing was performed in the same pressure condition as the above washing.

Subsequently, the aqueous acrylic acid solution was subjected to distillation. Even after the elapse of 120 days of continued distillation, absolutely no sign of increase in the pressure loss in the column and decrease in the coefficient of heat transfer of the shell-and-tube heat exchanger was observed. When the distillation was stopped and the interior of the distillation column was inspected, then absolutely no polymer of acrylic acid was observed.

In the present example, a more than equal effect of washing was obtained in about one half of the washing time required in Example 5.

Comparative Example 5

The distillation column was washed by following the procedure of Example 3 while omitting the pre-washing with water. When an aqueous 4% sodium hydroxide solution was supplied from the top of the column and the shell-and-tube heat exchanger annexed to the distillation column was operated to heat the aqueous 4% sodium hydroxide solution, then the polymer was swelled within 30 minutes of starting the heating and the distillation column was blocked and the washing could no longer be continued.

Example 8

The distillation column was washed by following the procedure of Example 3 while setting the pressure in the distillation column at 250 hPa, and the pre-washing time with water at 30 minutes.

Then, the crude butyl acrylate was subjected to distillation. Even after the elapse of 200 days of continued distillation, no sign of increase in the pressure loss within the column and decrease in the coefficient of heat transfer of the shell-and-tube heat exchanger was observed. The concentration of acrylic acid in the distilled butyl acrylate was not observed to increase. When the distillation was stopped and the interior of the distillation column was inspected, then absolutely no polymer of butyl acrylate was observed.

The entire disclosure of Japanese Patent Application No. 11-54316 filed on Mar. 2, 1999 including specification, claims, and summary are incorporated herein by reference in its entirety.

What is claimed is:

1. A method for removing solid substances adhered during production of (meth)acrylic acid, which comprises:
    washing a device constructed for the production thereof with a basic solution; and
    rinsing it with a solvent until the pH value of the waste water is not more than 9 at 50° C.
    for the purpose of removing solid substances such as polymer and precipitate formed during the course of the production, the solid substances being adhered to the surface of a flow way of the (meth)acrylic acid in the device;
    wherein removing of adhered solid substance is performed without overhauling of the device.

2. A method according to claim 1 further containing a pre-washing with a solvent prior to the washing with the basic solution.

3. A method for removing solid'substances adhered during production of a (meth)acrylic ester, which comprises:
    pre-washing a device constructed for the production thereof with a solvent,
    washing it with a basic solution; and
    rinsing it with a solvent until the pH value of the waste water is not more than 9 at 50° C.
    for the purpose of removing solid substances such as polymer and precipitate formed during the course of the production, the solid substances being adhered to the surface of a flow way of the (meth)acrylic ester in the device;

wherein removing of adhered solid substances is performed without overhauling of the device.

4. A method for removing solid substances adhered during production of (meth)acrylic acid and/or a (meth)acrylic ester, which comprises:

pre-washing a device constructed for the production thereof with a solvent washing it with a basic solution being a solution of at least one member selected from the group consisting of an oxide, hydroxide, carbonate, and hydrogen carbonate of an alkali metal and an oxide and hydroxide of an alkaline earth metal; and rinsing it with a solvent until the pH value of the waste water is not more than 9 at 50° C.

for the purpose of removing solid substances such as polymer and precipitate formed during the course of the production, the solid substances being adhered to the surface of a flow way of the (meth)acrylic acid and/or the (meth)acrylic ester in the device;

wherein removing of adhered solid substances is performed without overhauling of the device.

5. A method according to claim 4, wherein the basic solution is a solution of at least one member selected from the group consisting of an oxide, hydroxide, carbonate, and hydrogen carbonate of an alkali metal.

6. A method according to claim 5, wherein the basic solution is a solution of a hydroxide of an alkali metal.

7. A method according to claim 6, wherein the alkali metal is sodium or potassium.

8. A method according to claim 1, wherein the solvent is water.

9. A method according to claim 4, wherein the solvent to be used for the pre-washing and the rinsing is water.

10. A method according to claim 1, wherein the rinsing with water subsequent to the washing with the basic solution is continued until the total content of an alkali metal and alkaline earth metal in the waste water is not more than 50 mg/liter.

11. A method according to claim 10, wherein the rinsing is continued until the total content of the alkali metal and alkaline earth metal therein is not more than 10 mg/liter.

12. A method according to claim 9, wherein the water to be used for the rinsing has an electric conductivity of not more than 10 mS/m.

13. A method according to claim 12, wherein the water to be used for the rinsing has an electric conductivity of not more than 1 mS/m.

14. A method according claim 4, wherein the devices is selected from the group consisting of a distillation column, an absorption column, and a stripping column, and further includes accessories which are annexed thereto and pipes between therewith.

15. A method according to claim 4, wherein the washing with the basic solution and/or the rinsing with the solvent is performed under temperature(s) in the range of 50° C. to the boiling point thereof used.

16. A method according to claim 15, wherein the washing with the basic solution and/or the rinsing with the solvent is performed under temperature(s) in the range of 80° C. to the boiling point thereof used.

17. A method for removing solid substances adhered during production of (meth)acrylic acid and/or a (meth)acrylic ester, which comprises:

pre-washing a device constructed for the production thereof with a solvent washing it under a reduced pressure with a basic solution being a solution of at least one member selected from the group consisting of an oxide, hydroxide, carbonate, and hydrogen carbonate of an alkali metal and an oxide and hydroxide of an alkaline earth metal; and rinsing it with a solvent under a reduced pressure until the pH value of the waste water is not more than 9 at 50° C.

for the purpose of removing solid substances such as polymer and precipitate formed during the course of the production, the solid substances being adhered to the surface of a flow way of the (meth)acrylic acid and/or the (meth)acrylic ester in the device.

18. A method according to claim 17, wherein the reduced pressure is in the range of 100 to 900 hPa.

19. A method according to claim 17, wherein the reduced pressure is in the range of 150 to 300 hPa.

* * * * *